United States Patent [19]

Schirmer et al.

[11] Patent Number: 4,459,238

[45] Date of Patent: Jul. 10, 1984

[54] N-ARYLTHIOLCARBAMATES, HERBICIDES CONTAINING THEM, AND PROCESSES FOR COMBATING THE GROWTH OF UNWANTED PLANTS WITH THESE COMPOUNDS

[75] Inventors: Ulrich Schirmer, Heidelberg; Karl-Heinz Koenig, Frankenthal; Bruno Wuerzer, Otterstadt; Guenter Retzlaff, Roemerberg, all of Fed. Rep. of Germany

[73] Assignee: BASF Aktiengesellschaft, Fed. Rep. of Germany

[21] Appl. No.: 424,875

[22] Filed: Sep. 27, 1982

Related U.S. Application Data

[63] Continuation of Ser. No. 150,748, May 19, 1980, abandoned.

[30] Foreign Application Priority Data

May 25, 1979 [DE] Fed. Rep. of Germany ....... 2921130

[51] Int. Cl.³ .................................... C07C 155/08
[52] U.S. Cl. .................................... 260/455 A; 71/100
[58] Field of Search .................. 260/455 A; 71/100

[56] References Cited

U.S. PATENT DOCUMENTS

| | | | |
|---|---|---|---|
| 2,655,445 | 10/1953 | Todd | 71/120 |
| 2,863,899 | 12/1958 | Harris | 71/100 |
| 3,066,021 | 11/1962 | Beaver et al. | 71/100 |
| 3,318,947 | 5/1967 | Speziale et al. | 71/100 |
| 3,359,301 | 12/1967 | Speziale et al. | 71/100 |
| 3,852,319 | 12/1974 | Edamura et al. | 71/100 |
| 3,852,332 | 12/1974 | Cross et al. | 71/100 |

FOREIGN PATENT DOCUMENTS

| | | | |
|---|---|---|---|
| 1484461 | 5/1967 | France | 71/100 |
| 1250224 | 10/1971 | United Kingdom | 71/100 |

OTHER PUBLICATIONS

Ciba I, "Thiocarbanilate Esters, etc.;" (1960) CA 59, p. 2713g, (1963).
Baskakov et al., "Synthesis of Alkyl etc.;" (1966) CA 66, No. 55139y, (1967).

*Primary Examiner*—Glennon H. Hollrah
*Attorney, Agent, or Firm*—Keil & Weinkauf

[57] ABSTRACT

N-Arylthiolcarbamates for the formula

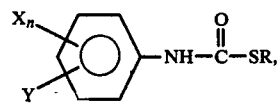

where R denotes methyl or ethyl, X denotes halogen, Y denotes alkyl, haloalkyl of at least 2 carbon atoms, alkoxyalkyl, cycloalkyl, alkoxy or halomethoxy, and n denotes one of the integers 1 and 2, herbicides containing these compounds, and their use as herbicides.

4 Claims, No Drawings

N-ARYLTHIOLCARBAMATES, HERBICIDES CONTAINING THEM, AND PROCESSES FOR COMBATING THE GROWTH OF UNWANTED PLANTS WITH THESE COMPOUNDS

This is a continuation of application Ser. No. 150,748, filed May 19, 1980, and now abandoned.

The present invention relates to novel N-arylthiolcarbamates, herbicides containing these compounds as active ingredients, and a process for combating unwanted plant growth with these compounds.

The herbicidal properties of S-methyl-N-(3-chlorophenyl)-thiolcarbamates have been disclosed (U.S. Pat. No. 2,863,899). This compound has only a poor herbicidal action on higher plants.

We have now found that novel N-arylthiolcarbamates of the formula

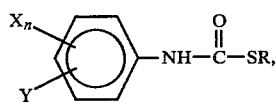

where R denotes methyl or ethyl, X denotes halogen (chlorine, bromine, fluorine, iodine), Y denotes alkyl (e.g., methyl, ethyl, isopropyl, t-butyl, n-hexyl), haloalkyl of at least 2 carbon atoms (e.g., 1-chloroisopropyl, 2-chloroethyl, chloro-tert-butyl), alkoxyalkyl (e.g., methoxymethyl, isopropoxymethyl, 2-methoxyethyl), cycloalkyl (e.g., cyclopropyl, cyclopentyl, cyclohexyl), alkoxy (e.g, methoxy, ethoxy, n-propoxy, isopropoxy), or halomethoxy (e.g., difluoromethoxy, trifluoromethoxy) and n denotes one of the integers 1 and 2, have a surprisingly good action on a number of broadleaved and grassy unwanted plants and are tolerated by crop plants.

The two processes described below are for instance suitable for the manufacture of the new compounds.

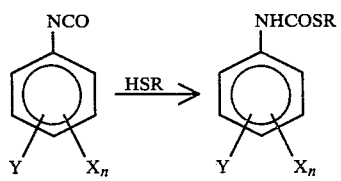

The reaction of aryl isocyanates with mercaptans takes place in the presence or the absence of a catalyst conventionally used for isocyanate reactions, e.g., tertiary amines (triethylamine, 1,4-diazabicyclo-(2,2,2)-octane, nitrogenous heterocycles (pyridine, 1,2-dimethylimidazole) or organic tin compounds (dibutyl tin diacetate, dimethyl tin dichloride), if desired in a solvent inert under the reaction conditions, for example hydrocarbons (e.g., ligroin, gasoline, toluene, pentane, cyclohexane), halohydrocarbons (e.g., methylene chloride, chloroform, dichloroethane, chlorobenzene, o-, m- and p-dichlorobenzene), nitrohydrocarbons (e.g., nitrobenzene, nitromethane), nitriles (e.g., acetonitrile, butyronitrile, benzonitrile), ethers (e.g., diethyl ether, tetrahydrofuran, dioxane), esters (e.g., ethyl acetate, methyl propionate), ketones (e.g., acetone, methyl ethyl ketone) or amides (e.g., dimethylformamide, formamide), at from $-30°$ to $+150°$ C., preferably from $0°$ to $40°$ C., in equivalent amounts or with one of the reactants in excess (S. Petersen, Methoden der Organ. Chemie, VIII, p. 131, Georg Thieme-Verlag, Stuttgart, 4th ed., 1952).

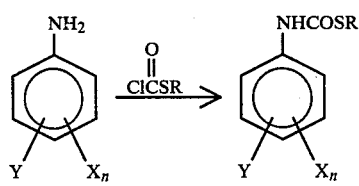

Aromatic amines are reacted with thio chloroformates in a solvent, e.g., water, alcohols (e.g., methanol, ethanol, isopropanol) or as given under A, with the aid of a conventional acid binder, e.g., alkali metal hydroxides, carbonates or bicarbonates, alkaline earth metal oxides, hydroxides, carbonates or bicarbonates, or tertiary organic bases (e.g., triethylamine, pyridine, N,N-dimethylaniline, N,N-dimethylcyclohexylamine, quinoline and tributylamine), at from $-20°$ to $+150°$ C., preferably from $20°$ to $60°$ C. Process B is preferred (German Laid-Open Application DE-OS No. 1,643,763).

The preparation of the novel N-arylthiolcarbamates is illustrated by the following examples.

EXAMPLE 1

At $0°$ C., a solution of 4.1 parts by weight of methylmercaptan and one drop of triethylamine in 40 parts by weight of acetonitrile is dripped into a solution of 12.5 parts by weight of 3-methyl-4-fluorophenyl isocyanate in 200 parts by weight of toluene. The mixture is slowly allowed to heat up to room temperature, the solvents are evaporated in a rotary evaporator, and the residue is recrystallized from cyclohexane. White crystals are obtained which melt at $98°–99°$ C. (no. 1).

The compound has the following structural formula:

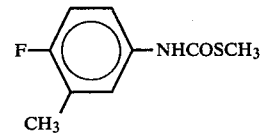

EXAMPLE 2

100 parts by weight of sodium bicarbonate is added to 135 parts by weight of 3-chloro-4-isopropylaniline in 1,000 parts by weight of tetrahydrofuran. While stirring, 89 parts by weight of thiomethyl chloroformate is dripped in at room temperature ($20°$ C.), the mixture is stirred for a further 16 hours at room temperature and then filtered, the solvent is distilled off in a rotary evaporator, and petroleum ether is added to the oil which is obtained. The crystals which form are filtered off and dried; m.p.: $116°–118°$ C. (no. 2).

The compound has the following structural formula:

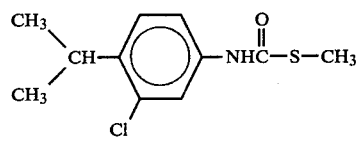

The following N-arylthiolcarbamates may be prepared analogously:

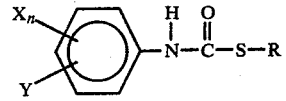

| No. | X | Y | R | m.p. °C. |
|---|---|---|---|---|
| 3 | 3-Cl | 4-CH(CH$_3$)$_2$ | C$_2$H$_5$ | highly viscous oil |
| 4 | 3-Cl | 4-CH$_3$ | CH$_3$ | 112–113 |
| 5 | 4-Cl | 3-CH$_3$ | CH$_3$ | 105–107 |
| 6 | 3-Br | 4-CH(CH$_3$)$_2$ | CH$_3$ | |
| 7 | 3-F | 4-CH(CH$_3$)$_2$ | CH$_3$ | |
| 8 | 3-I | 4-CH(CH$_3$)$_2$ | CH$_3$ | |
| 9 | 3-Cl | 4-cyclo C$_5$H$_9$ | CH$_3$ | |
| 10 | 3-Cl | 4-CH$_2$CH$_2$Cl | CH$_3$ | |
| 11 | 3-Cl | 4-C$_2$H$_5$ | CH$_3$ | 93–95 |
| 12 | 4-F | 3-CH$_3$ | C$_2$H$_5$ | |
| 13 | 3-Cl | 5-CH$_3$ | CH$_3$ | 127–129 |
| 14 | 3-Br | 4-CH(CH$_3$)$_2$ | C$_2$H$_5$ | |
| 15 | 3-I | 4-C$_2$H$_5$ | CH$_3$ | |
| 16 | 3-I | 4-C(CH$_3$)$_3$ | C$_2$H$_5$ | |
| 17 | 3-Cl | 4-cyclo C$_6$H$_{11}$ | CH$_3$ | |
| 18 | 3-Cl | 4-CH(CH$_3$)(CH$_2$Cl) | CH$_3$ | 77–79 |
| 19 | 3-Cl | 4-CH$_2$CH$_2$Cl | C$_2$H$_5$ | |
| 20 | 4-I | 2-CH$_3$ | CH$_3$ | |
| 21 | 3-Cl | 4-CH(CH$_3$)(CH$_2$OCH$_3$) | CH$_3$ | |
| 22 | 3-Br | 4-CH$_3$ | CH$_3$ | |
| 23 | 3-Cl | 4-cyclo C$_3$H$_5$ | CH$_3$ | |
| 24 | 3-F | 4-CH$_3$ | CH$_3$ | 122–124 |
| 25 | 3-Cl | 4-C(CH$_3$)$_3$ | CH$_3$ | 125–127 |
| 26 | 2-F | 4-CH$_3$ | CH$_3$ | |
| 27 | 3-Br | 4-CH$_2$OCH$_3$ | CH$_3$ | |
| 28 | 4-Cl | 3-CH$_2$OC(CH$_3$)$_3$ | CH$_3$ | |
| 29 | 3-Cl | 4-i-C$_5$H$_{11}$ | CH$_3$ | 74–76 |
| 30 | 4-Cl | 3-CH(CH$_3$)$_2$ | CH$_3$ | |
| 31 | 4-Br | 3-CH$_2$OC(CH$_3$)$_3$ | CH$_3$ | |
| 32 | 3-Cl | 4-CH$_2$OCH(CH$_3$)$_2$ | CH$_3$ | |
| 33 | 3-Br | 4-CH$_2$OCH(CH$_3$)$_2$ | CH$_3$ | |
| 34 | 3-Br | 4-n-C$_3$H$_7$ | CH$_3$ | |
| 35 | 4-Cl | 3-C(CH$_3$)$_3$ | CH$_3$ | |
| 36 | 4-Br | 3-CH(CH$_3$)$_2$ | CH$_3$ | |
| 37 | 4-Cl | 3-CH$_2$OCH$_3$ | CH$_3$ | |
| 38 | 3-Cl | 4-CH(CH$_3$)(C$_2$H$_5$) | CH$_3$ | 83–85 |
| 39 | 4-Cl | 3-C$_2$H$_5$ | CH$_3$ | |
| 40 | 3-Br | 4-C$_2$H$_5$ | CH$_3$ | |
| 41 | 3-Br | 4-C(CH$_3$)$_2$(C$_2$H$_5$) | CH$_3$ | |
| 42 | 4-Br | 3-CH$_3$ | CH$_3$ | 97–99 |
| 43 | 3-Cl | 4-CH$_2$CH$_2$OCH$_3$ | CH$_3$ | |
| 44 | 3-Cl | 4-n-C$_3$H$_7$ | CH$_3$ | |
| 45 | 3-Br | 4-CH$_2$CH$_2$OCH$_3$ | CH$_3$ | |
| 46 | 3-Br | 4-C(CH$_3$)$_3$ | CH$_3$ | |
| 47 | 2-F | 5-CH$_3$ | CH$_3$ | |
| 48 | 3-Cl | 4-CH(CH$_3$)(C$_2$H$_5$) | C$_2$H$_5$ | 70–72 |
| 49 | 3-Cl | 4-n-C$_4$H$_9$ | CH$_3$ | |
| 50 | 3-Br | 4-cyclo C$_5$H$_{11}$ | CH$_3$ | |
| 51 | 3-Cl | 4-C(CH$_3$)$_2$(C$_2$H$_5$) | CH$_3$ | |
| 52 | 2-F | 5-C(CH$_3$)$_3$ | CH$_3$ | 38–40 |
| 53 | 3-Cl | 4-n-C$_5$H$_9$ | CH$_3$ | |
| 54 | 3-Cl | 4-OCF$_2$H | CH$_3$ | 98–100 |
| 55 | 3-Cl | 4-OCF$_3$ | CH$_3$ | |
| 56 | 4-Cl | 3-OCF$_2$H | CH$_3$ | |
| 57 | 3-Cl | 4-OCH$_3$ | CH$_3$ | 130–132 |
| 58 | 3-Br | 4-OCH$_3$ | CH$_3$ | |
| 59 | 3-Cl | 4-OC$_2$H$_5$ | CH$_3$ | |
| 60 | 3-Cl, 4-Cl | 5-CH$_3$ | CH$_3$ | 144–146 |
| 61 | 3-Cl | 4-OCF$_3$ | C$_2$H$_5$ | |
| 62 | 3-Cl | 4-O—i-C$_3$H$_7$ | CH$_3$ | 108–109 |
| 63 | 3-Cl | 4-O—n-C$_3$H$_7$ | CH$_3$ | 104–106 |
| 64 | 3-Cl | 4-O—i-C$_3$H$_7$ | C$_2$H$_5$ | |
| 65 | 3-Cl | 4-O—n-C$_3$H$_7$ | C$_2$H$_5$ | |
| 66 | 3-Cl, 5-Cl, | 4-OCH$_3$ | CH$_3$ | 162–164 |
| 67 | 3-Cl | 4-OCHF$_2$ | C$_2$H$_5$ | |
| 68 | 3-Br | 4-OC$_2$H$_5$ | CH$_3$ | |
| 69 | 3-Br | 4-O—n-C$_3$H$_7$ | CH$_3$ | |
| 70 | 3-Br, 5-Cl, | 4-OCH$_3$ | CH$_3$ | 161–163 |
| 71 | 3-Br | 4-O—i-C$_3$H$_7$ | CH$_3$ | |

The influence of various representatives of the compounds according to the invention on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants (cf. Table 1) were sown shallow, and separately, according to species, and the plants were grown to a height of 3 to 10 cm before being treated. Certain test plant species were first grown as seedlings in special seedling containers before being transferred to the abovementioned vessels. The plants were treated with the chemical agents a few days after they had taken root. The compounds were emulsified or suspended in water as vehicle, and sprayed through finely distributing nozzles onto the plants. The pots were set up in the greenhouse—species from warmer areas at from 25° to 40° C., and species from moderate climates at 15° to 30° C. The experiments were run for from 3 to 6 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The tables which follow demonstrate the selective herbicidal action of the compounds according to the invention. They are applied predominantly postemergence, but an action on preemergence application (i.e., before the plants germinate) is also evident.

A special application technique is to spray to active ingredients weith the aid of spraying equipment in such a way that the leaves of sensitive crop plants are if possible not hit; the active ingredients reach the soil or unwanted plants growing below the crop plants (post-directed, lay-by treatment). The application rates vary, depending on season and growth stage, from 0.1 to 15 kg/ha and more; higher rates are particularly suitable for total elimination of vegetation.

The herbicidal agents contain from 0.5 to 95, and preferably from 1 to 90, wt% of active ingredient.

In view of the many application methods possible, the agents according to the invention, or mixtures containing them, may be used in addition to the crop plants listed in the tables in a large number of other crops for eliminating unwanted growth.

The following crop plants are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |

| Botanical name | Common name |
|---|---|
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffes canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispsa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. *vulgare*) | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

The new arylthiolcarbamates may be mixed with each other, or with numerous representatives of other herbicidal or growth-regulating active ingredient groups, and applied in such combinations. These combinations extend the spectrum of action, and synergistic effects are sometimes achieved. Examples of compounds which may be admixed are diazines, N-phenylcarbamates, thiolcarbamates, diurethanes, halocarboxylic acids, phenoxy fatty acids, triazines, amides, ureas, diphenyl ethers, triazinones, uracils, benzofuran derivatives, etc. A number of active ingredients which, together with the new compounds, give mixtures useful for widely varying applications are listed below by way of example.

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-,$\alpha,\alpha,\beta,\beta$-tetrafluoroethoxyphenyl)-3(2H)-pyridazinone
5-dimethylamino-4-chloro-2-phenyl-3(2H)-pyridazinone
4,5-dimethyl-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoylpropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate
methyl N-3-(4'-fluorophenoxycarbonylamino)-phenyl-thiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid, (salts, esters, amides)
2,3,6-trichlorobenzoic acid, (salts, esters, amides)
2,3,5,6-tetrachlorobenzoic acid, (salts, esters, amides)
2-methoxy-3,6-dichlorobenzoic acid, (salts, esters, amides)
2-methoxy-3,5,6-trichlorobenzoic acid, (salts, esters, amides)
3-amino-2,5,6-trichlorobenzoic acid, (salts, esters, amides)
O,S-dimethyltetrachlorothioterephthalate
dimethyl-2,3,5,6-tetrachloroterephthalate
disodium 3,6-endooxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine 2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid-3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylaminophenylacetamide
N-4-methyl-5-(trifluoromethyl)-sulfonylaminophenylacetamide
2-propionylamino-4-methyl-5-chlorothiazole
O-(methylsulfonyl)-glycolic acid-N-ethoxymethyl-2,6-dimethylanilide
O-(methylaminosulfonyl)-glycolic acid-N-isopropylanilide
O-(isopropylaminosulfonyl)-glycolic acid-N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,O,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea 1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid, (salts, esters, amides)
4-chlorophenoxyacetic acid, (salts, esters, amides)
2,4-dichlorophenoxyacetic acid, (salts, esters, amides)
2,4,5-trichlorophenoxyacetic acid, (salts, esters, amides)
2-methyl-4-chlorophenoxyacetic acid, (salts, esters, amides)
3,5,6-trichloro-2-pyridinyl-oxyacetic acid, (salts, esters, amides)
methyl α-naphthoxyacetate
2-(2-methylphenoxy)-propionic acid, (salts, esters, amides)
2-(4-chlorophenoxy)-propionic acid, (salts, esters, amides)
2-(2,4-dichlorophenoxy)-propionic acid, (salts, esters, amides)
2-(2,4,5-trichlorophenoxy)-propionic acid, (salts, esters, amides)
2-(2-methyl-4-chlorophenoxy)-propionic acid, (salts, esters, amides)
4-(2,4-dichlorophenoxy)-butyric acid, (salts, esters, amides)
4-(2-methyl-4-chlorophenoxy)-butyric acid, (salts, esters, amides)
cyclohexyl-3-(2,4-dichlorophenoxy)-acrylate
9-hydroxyfluorenecarboxylic acid-(9), (salts, esters)
2,3,6-trichlorophenylacetic acid, (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole, (salts)
1,2,3,6-tetrahydropyridazine-3,6-dione, (salts)
succinic acid mono-N-dimethylhydrazide, (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide.

It may also be useful to apply the active ingredients, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Oils and oil concentrates of various types, wetting agents, spreader-stickers and antifoams may be added to the individual active ingredients or mixtures thereof.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

TABLE 1

List of plant names

| Botanical name | Abbreviation in tables | Common name |
|---|---|---|
| *Amaranthus retroflexus* | Amar. retr. | redroot pigweed |
| *Arachys hypogaea* | | peanuts (groundnuts) |
| *Avena fatua* | | wild oats |
| *Brassica napus* | | rape (turnips) |
| *Centaurea cyanus* | | cornflower |
| *Digitaria sanguinalis* | Digit. sang. | large crabgrass |
| *Euphorbia geniculata* | Euphorb. genic. | South American member of the spurge family |
| *Glycine max* | | soybeans |
| *Gossypium hirsutum* | | cotton |
| *Lolium multiflorum* | | Italian ryegrass |
| *Nicandra physaloides* | Nicandra physal. | apple-of-Peru |
| *Oryza sativa* | | rice |
| *Pisum sativum* | | English peas |
| *Poa annua* | | annual bluegrass |
| *Sesbania exaltata* | | hemp sesbania (coffeeweed) |
| *Solanum nigrum* | Solan. nigr. | black nightshade |
| *Sorghum bicolor* | | sorghum |
| *Stellaria media* | | chickweed |
| *Triticum aestivum* | Tritic. aest. | wheat |

Table 2

New thiolcarbamates as selective herbicides; postemergence treatment in the greenhouse

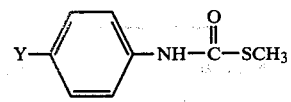

| Compounds no. | Substituents X | Y | kg/ha | *Arachia hypogaca* | *Brassica napus* | Tritic. aest. | Amar. retr. | Digit. sang. | Euphorb. genic. | Nicandra physal. | Solan. nigr. | Stellaria media |
|---|---|---|---|---|---|---|---|---|---|---|---|---|
| 2 | Cl | C₃H₇i | 0.5 | 5 | 5 | 13 | 100 | 100 | 80 | 100 | 84 | 98 |
|   |    |       | 1.0 | 5 | 12 | 15 | 100 | 100 | 83 | 100 | 99 | 98 |
|   | Cl | H | 0.5 | 0 | 30 | 40 | 30 | 40 | 0 | 20 | 0 | 40 |
|   | (prior art) | | 1.0 | 0 | 30 | 50 | 80 | 40 | 10 | 25 | 0 | 40 |

0 = no damage
100 = plants destroyed

TABLE 3

Selective control of unwanted plants in Leguminosae; postemergence treatment in the greenhouse
Compound no. 18
Appln. rate 0.25 kg/ha

| Test plants | Damage % |
|---|---|
| *Arachis hypogaea* | 0 |
| *Glycine max* | 10 |
| *Amaranthus retroflexus* | 100 |
| *Centaurea cyanus* | 90 |
| *Digitaria sanguinalis* | 80 |
| *Euphorbia geniculata* | 100 |
| *Poa annua* | 95 |
| *Sesbania exaltata* | 100 |
| *Stellaria media* | 98 |

0 = no damage
100 = plants destroyed

TABLE 4

Control of *Sesbania exaltata* in various crops; postemergence treatment in thew greenhouse
Compound no. 1

| | Damage % | |
|---|---|---|
| Test plants | Appln. rate 0.25 | 0.5 kg/ha |
| *Arachia hypogaea* | 0 | 0 |

TABLE 4-continued

Control of *Sesbania exaltata* in various crops;
postemergence treatment in thew greenhouse
Compound no. 1

| Test plants | Appln. rate | Damage % 0.25 | 0.5 kg/ha |
|---|---|---|---|
| Glycine max | | 0 | 0 |
| Oryza sativa | | 0 | 0 |
| Pisum sativum | | 10 | 15 |
| Sorghum bicolor | | 0 | 15 |
| Sesbania exaltata | | 100 | 100 |

0 = no damage
100 = plants completely destroyed

TABLE 5

Selective weed control in Leguminosae;
postemergence treatment in the greenhouse
Compound no. 29

| Test plants | Damage (%) at 0.5 kg/ha |
|---|---|
| Arachis hypogaea | 0 |
| Glycine max | 10 |
| Pisum sativum | 10 |
| Amaranthus retroflexus | 100 |
| Centaurea cyanus | 80 |
| Digitaria sanguinalis | 90 |
| Poa annua | 90 |
| Sesbania exaltata | 100 |
| Stellaria media | 98 |

0 = no damage
100 = plants completely destroyed

TABLE 6

Selective control of unwanted plants;
postemergence treatment in the greenhouse
Compound no. 54

| Test plants | Damage (%) at 0.5 kg/ha |
|---|---|
| Arachis hypogaea | 0 |
| Gossypium hirsutum | 0 |
| Amaranthus retroflexus | 100 |
| Avena fatua | 80 |
| Digiteria sanguinalis | 100 |
| Euphorbia geniculata | 100 |
| Nicandra physaloides | 100 |
| Sesbania exaltata | 100 |
| Solanum nigrum | 100 |
| Stellaria media | 98 |

0 = no damage
100 = plants completely destroyed

TABLE 7

Herbicidal action of further compounds;
postemergence treatment in the greenhouse

| Compound no. | kg/ha | Test plants and damage (%) | | |
|---|---|---|---|---|
| | | Ipomoea spp. | Centaurea cyanus | Lolium multiflorum |
| 5 | 3.0 | — | 90 | — |
| 25 | 3.0 | 90 | 100 | 80 |
| 42 | 3.0 | — | 90 | 100 |
| 57 | 3.0 | 90 | 90 | 90 |
| 62 | 3.0 | 95 | 100 | — |
| 63 | 3.0 | — | 90 | 90 |

0 = no action
100 = plants completely destroyed

EXAMPLE 3

90 parts by weight of compound 1 is mixed with 10 parts by weight of N-methyl-α-pyrrolidone. A mixture is obtained which is suitable for application in the form of very fine drops.

EXAMPLE 4

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 5

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 6

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 3 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 8

3 parts by weight of compound 3 is intimately mixed with 97 parts by weight of particulate kaolin. A dust is obtained containing 3% by weight of the active ingredient.

EXAMPLE 9

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 10

40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

EXAMPLE 11

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An N-arylthiolcarbamate of the formula

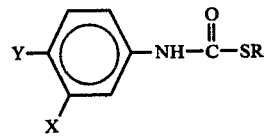

where R denotes methyl or ethyl, X denotes halogen and Y denotes alkyl of 2 to 6 carbon atoms, haloalkyl of 2 to 4 carbon atoms, methoxy, ethoxy, n-propoxy, isopropoxy, difluoromethoxy and trifluoromethoxy.

2. An N-arylthiolcarbamate selected from the group consisting of S-methyl-N-(3-chloro-4-isopropylphenyl)-thiolcarbamate, S-methyl-N-(3-chloro-4-(1-chloroisopropyl)-phenyl)-thiolcarbamate and S-methyl-N-(3-chloro-4-(difluoromethoxy)-phenyl)-thiolcarbamate.

3. The compound of claim 2 which is S-methyl-N-(3-chloro-4-(isopropylphenyl)-thiolcarbamate.

4. The compound of claim 2 which is S-methyl-N-(3-chloro-4-(difluoromethoxy)-phenyl)-thiolcarbamate.

* * * * *